(12) United States Patent
Letelier Munoz et al.

(10) Patent No.: US 8,852,654 B2
(45) Date of Patent: Oct. 7, 2014

(54) **USE OF A STANDARDISED DRY EXTRACT OF LEAVES OF *BUDDLEJA GLOBOSA* HOPE, BG-126, FOR THE TREATMENT AND PREVENTION OF GASTROINTESTINAL DISORDERS CAUSED BY TREATMENT WITH NITROFURANTOIN AND OTHER ANTIMICROBIALS**

(76) Inventors: Maria Eugenia Letelier Munoz, Santiago (CL); Enrique Antonio Ossandon Salas, Santiago (CL)

( * ) Notice: Subject to any disclaimer, the term of this patent is extended or adjusted under 35 U.S.C. 154(b) by 0 days.

(21) Appl. No.: 13/982,005

(22) PCT Filed: Jan. 27, 2012

(86) PCT No.: PCT/CL2012/000001
§ 371 (c)(1),
(2), (4) Date: Oct. 1, 2013

(87) PCT Pub. No.: WO2012/100365
PCT Pub. Date: Aug. 2, 2012

(65) Prior Publication Data
US 2014/0017344 A1    Jan. 16, 2014

(30) Foreign Application Priority Data
Jan. 28, 2011   (CL) ..................................... 183-2011

(51) Int. Cl.
*A01N 65/00*      (2009.01)
*A61K 36/80*      (2006.01)
*A61K 36/00*      (2006.01)
*A61K 31/44*      (2006.01)
*A61K 31/4178*    (2006.01)

(52) U.S. Cl.
CPC ................. *A61K 36/80* (2013.01); *A61K 36/00* (2013.01); *A61K 31/44* (2013.01); *A61K 31/4178* (2013.01)
USPC ........................................................ 424/725

(58) Field of Classification Search
None
See application file for complete search history.

(56) References Cited

PUBLICATIONS

Molares S. et al., "Ethnobotanical review of the Mapuche medicinal flora: Use patterns on a regional scale",(2009), Journal of Ethnopharmacology, vol. 122, pp. 251-260.*

* cited by examiner

*Primary Examiner* — Michael Meller
(74) *Attorney, Agent, or Firm* — Gottlieb, Rackman & Reisman PC (57) ABSTRACT

The invention relates to the use of a composition comprising extract of *Buddleja globosa* Hope and pharmacologically accepted excipients for the preparation of a phyto-pharmaceutical agent, a drug or a nutraceutical for the prevention of gastrointestinal disorders, particularly those associated with treatment with nitrofurantoin or gastric disorders produced by ulcers, gastric diseases or damage to the gastrointestinal tract. The aforementioned disorders can correspond to abdominal pain, dyspepsia, nausea, vomiting, diarrhea, constipation, inflammation and cephalalgia resulting from treatment with nitrofurantoin and other antimicrobials. In addition, the extract and the compositions thereof can be used to enhance the antibacterial action of nitrofurantoin, particularly against *Escherichia coli*.

10 Claims, 9 Drawing Sheets

|  |  | Group 1 | | Group 2 | |
|---|---|---|---|---|---|
| Parameter | Reference values | Mean Day 1 n =15 (± SD) | Mean Day 11 n = 15 (± SD) | Mean Day 1 n = 15 (± SD) | Mean Day 11 n = 15 (± SD) |
| Red series | | | | | |
| Erythrocytes (M/μL) | 4.5 – 4.9 | 4.5 ± 0.33 | 4.4 ± 0.473 | 4.3 ± 0.42 | 4.4 ± 0.34 |
| Hematocrit (%) | 37 – 47 | 39± 2.8 | 38 ± 4.2 | 38 ± 3.9 | 39 ± 3.0 |
| Hemoglobin (g/dL) | 12 – 16 | 13 ± 1.0 | 13 ± 1.5 | 13 ± 1.4 | 13 ± 1.1 |
| MCV (fL) | 82 – 95 | 87 ± 4.6 | 87 ± 5.0 | 87 ± 5.0 | 88 ± 3.6 |
| MCH (pg) | 27 – 31 | 30 ± 1.5 | 30 ± 1.8 | 30 ± 2.0 | 30 ± 1.5 |
| MCHC (g/dL) | 32 – 36 | 34 ± 0.7 | 34± 0.9 | 34 ± 0.9 | 34 ± 0.7 |
| ANC |  | 3,986 ± 1277 | 3,485 ± 1222 | 3,868 ± 1100 | 3,443 ± 1413 |
| Platelets (/μL) | 150,000 – 400,000 | 261,733 ± 103,260 | 264,833 ± 73,285 | 274,600 ± 118,405 | 282,083 ± 103,069 |
| ESR (mm/hr) | 0 – 30 | 30 ± 18.1 | 30 ± 15.6 | 25 ± 20.9 | 22 ± 17.3 |
| White Series | | | | | |
| Leukocytes (/μL) | 4.000 – 10.000 | 6,773 ± 1,726 | 6,050 ± 1,817 | 6,913 ± 1,764 | 6,525 ± 2,101 |
| Segmented |  | 58.3 ± 6.90 | 57.2 ± 8.10 | 55.7 ± 5.94 | 52.4 ± 8.78 |
| Eosinophils |  | 2.5 ± 1.36 | 3.7 ± 2.39 | 3.3 ± 1.58 | 3.4 ± 1.97 |
| Monocytes |  | 7.6 ± 2.47 | 7.0 ± 1.13 | 7.0 ± 1.60 | 6.5 ± 1.78 |
| Lymphocytes |  | 31.3 ± 6.14 | 32.2 ± 9.11 | 33.8 ± 6.75 | 37.1 ± 9.62 |

Figure 7

|  |  | Group 1 | | Group 2 | |
|---|---|---|---|---|---|
| Parameter | Reference values | Mean Day 1 n = 15 (± SD) | Mean Day 11 n = 15 (± SD) | Mean Day 1 n = 15 (± SD) | Mean Day 11 n = 15 (± SD) |
| Glucose (mg/dL) | 74 – 100 | 105 ± 65.9 | 120 ± 72.3 | 84 ± 11.2 | 85 ± 10 |
| Ureic nitrogen (mg/dL) | 7 – 17 | 16 ± 6.35 | 16 ± 3.6 | 14 ± 3.9 | 13 ± 3.1 |
| Uric acid (mg/dL) | 2.5 - 7.5 | 4.7 ± 1.04 | 4 ± 0.54 | 4 ± 1.10 | 3.9 ± 1.38 |
| Calcium (mg/dL) | 8.4 - 10.2 | 9.5 ± 0.65 | 9.5 ± 0.59 | 9.3 ± 0.21 | 9.2 ± 0.25 |
| Phosphorus (mg/dL) | 2.5 - 4.5 | 3.9 ± 0.44 | 3.9± 0.99 | 4.2 ± 0.53 | 4.1 ± 0.47 |
| Total proteins (g/dL) | 6.3 - 8.2 | 7.3 ± 0.42 | 7.2 ± 0.42 | 7.5 ± 0.52 | 7.6 ± 0.40 |
| Albumin (g/dL) | 3.5 - 5.0 | 4.3 ± 0.30 | 4.3 ± 0.24 | 4.3 ± 0.31 | 4.4 ± 0.31 |
| Total Cholesterol (mg/dL) | Menor a 200 | 196 ± 31.3 | 185 ± 38.6 | 190 ± 36.5 | 186 ± 31.4 |
| Total bilirubin (mg/dL) | 0.2 - 1.3 | 0.4 ± 0.17 | 0.4 ± 0.16 | 0.5 ± 0.38 | 0.6 ± 0.33 |
| Oxalacetic Transaminase (GOT) (U/L) | 13 - 36 | 32 ± 13.6 | 29 ± 11.4 | 27 ± 11.6 | 30 ± 8.4 |
| Total alkaline phosphatase (FAT) (U/L) | 38 – 126 | 119 ± 31.4 | 108 ± 18.6 | 107 ± 35.0 | 108 ± 33.7 |
| Total Lactate Dehydrogenase (LDH) (U/L) | 313 – 618 | 492 ± 75.4 | 502.1 ± 113.7 | 514 ± 136.4 | 508 ± 137.5 |

Figure 8

|  | Group 1 | | Group 2 | |
| --- | --- | --- | --- | --- |
| Parameter | Mean Day 1<br>n = 15 (± SD) | Mean Day 11<br>n = 15 (± SD) | Mean Day 1<br>n = 15 (± SD) | Mean Day 11<br>n = 15 (± SD) |
| FRAP | 292 ± 40.9 | 280.3 ± 58.3 | 282.5 ± 66.7 | 278.5 ± 52.5 |
| MDA | 0.73 ± 0.32 | 0.71 ± 0.17 | 0.71 ± 0.21 | 0.76 ± 0.35 |

Figure 9

USE OF A STANDARDISED DRY EXTRACT OF LEAVES OF *BUDDLEJA GLOBOSA* HOPE, BG-126, FOR THE TREATMENT AND PREVENTION OF GASTROINTESTINAL DISORDERS CAUSED BY TREATMENT WITH NITROFURANTOIN AND OTHER ANTIMICROBIALS

FIELD OF THE INVENTION

This invention relates to the use of a composition containing extracts of *Buddleja globosa* Hope and pharmacologically accepted additives for the treatment or prevention of several gastrointestinal disorders, particularly those associated with patient treatment with nitrofurantoin.

BRIEF DESCRIPTION OF THE INVENTION

The present invention is related to the use of a composition containing extracts of *Buddleja globosa* Hope and pharmacologically accepted additives for the preparation of a phytopharmaceutical agent, a medicine or a nutraceutical agent, for prevention of gastrointestinal disorders, particularly those associated to the treatment with nitrofurantoin or other gastric disorders produced by ulcers, gastric pathologies or damage to the gastric tissue. The disorders can include abdominal pains, dyspepsia, nausea, vomit, diarrhea, constipation, inflammation and migraine derived from the treatment with nitrofurantoin or other antimicrobial agents. In addition, the extract and its compositions are useful to potentiate the antibacterial action of nitrofurantoin, especially against *Escherichia coli*.

In the preferred embodiment, matico (*Buddleja globosa*) extract is used as the primary ingredient for treatment. The treatment may be in the form of a liquid or a solid. In the preferred administration, each unit of administration contains from 250 to 550 mg of *Buddleja globosa*, administration is preferably from 1 to 2 units but no more than 5 units per day, for a duration of preferably 3 to 10 days, although the range of days may be extended based on patient response.

DISCUSSION OF PRIOR ART

A urinary infection or urinary tract infection (UTI), is the existence of pathogenic microbial agents in urine, urethra, bladder, kidney or prostate typically caused by an obstruction of the urinary flow, vesico-urethral reflux, residual urine, diabetes, pregnancy, immunosuppression, aging and previous infections. Symptoms accompanying these infections may include increased urinary frequency, dysuria (painful urination) or urinary urgency (sensation of incomplete urination, with persistence of the previous symptoms). Nevertheless, these infections also can be asymptomatic.

The UTI can be divided into two anatomical categories: lower UTI (urethritis, cystitis and prostatitis) and higher UTI (acute pyelonephritis, renal abscess and perinephric abscess). Lower UTI is very common and widely affects the population, from younger children to older adults [Lee et al, 2007]. The incidence of this disease is increased by age due to alterations such as decreased cellular immunity, decreased defenses of bladder followed by obstructive uropathy, neurogenic bladder dysfunction and increase of the receptivity of the uroepithelial cells towards bacteria [Richards C., 2004]. These infections are caused by *Escherichia coli* (70-95%) and to a minor extent, by *Proteus mirabilis*, *Klebsiella* spp. and *Staphylococcus saprophyticus* [Guay D., 2008]. All over the world, the percentage of UTI by *E. coli* in adults is about 75% [Bishop M., 2004].

Mainly women are affected by these infections, with a 50-70% risk and 20-30% of risk of recurrence during life at least once. This is due to the anatomy of women's urinary routes (shorter urethra and its proximity with the anus). In older women, recurrence of this disease increases because defenses against infections are decreased and in addition, because they are affected by other pathologies like urinary incontinence and/or diabetes, diseases that increase the risk of UTI [Lee et al, 2007]. The great majority of the recurrences take place by re-infection caused by bacteria from the normal intestinal flora, like *E. coli* [Bishop M., 2004]. This fact has forced the medical community to prescribe antibiotics in low doses as prophylactic measures.

In Chile, this kind of infection is of public interest due to development of antibiotic resistance and recurrence to the infection [Guay D., 2008; Courteous et al, 2007]. In women, UTI occurs in high frequency, with an annual incidence from 10 to 15% [Guay D., 2008]. In fact, 40 to 50% of the women could suffer at least one low UTI along their life [Courteous et al, 2007]. In addition, low UTI are also an important problem for the geriatric public health. Finally, the recurrence of low UTI in the Chilean women population (~30%) is an additional problem of public health, reaching 53% in women over 55 years of age [Valdevenito J., 2008]. This recurrence is mainly due to re-infection, not only by the development of bacterial resistance to antibiotics, but also to a higher receptivity of the uroepithelial cells to these bacteria in certain individuals [Valdevenito J., 2008]. A study performed in Chile between January and September of 2005 showed that *E. coli* was responsible for 88.5% of the UTI cases in patients with an average of 52 years old. Worldwide, the percentage of UTI by *E. coli* in adults is about 75% [Bishop M., 2004; Cortés et al, 2007; Valdebenito J., 2008].

General treatment for UTI is the administration of antimicrobial agents in periods of 3 to 7 days. Most commonly used antimicrobial agents are clotrimoxazole (sulphamethoxazole+trimethoprim), ciprofloxacin, nitrofurantoin and some cephalosporins. Choice of the best antimicrobial agent not only depends on the class agent, but also on the prevalence of the resistance, potential adverse effects, pharmacokinetics and the population to be treated [Nicolle L., 2002].

Among these drugs, nitrofurantoin is one of the most prescribed in Chile [Valdevenito J., 2008]. This is because nitrofurantoin is one of the few bactericidal drugs which have maintained its efficacy for low UTI, in contrast to clotrimoxazole, amoxicillin and ampicillin [Cortés et al, 2007].

Nitrofurantoin: Adverse Reactions

Nitrofurantoin (N-(5-nitro-2-furfuriliden)-1-aminohidantoin) has been for more than 50 years, one of the drugs of choice for the treatment of uncomplicated UTI, because it is effective against infections caused by *E. coli*, *S. saprophyticus* and *K. pneumoniae*. Moreover, it is used as prophylactic therapy against recurrent UTI, since it appears to reduce re-infections by 95%. Over the last few decades, use of this drug in this indication has decreased continuously, due to the development of other antimicrobial agents more suitable for UTI. However, because as *E. coli* rapid resistance grows to standard drugs, low resistance rates generated by nitrofurantoin in the population and its lower price, currently these drugs represent an excellent therapeutic alternative, in spite of its known side effects [Cortés et al, 2007].

The mechanism of action of nitrofurantoin is not well known. In this regard, there are several reports suggesting that nitrofurantoin inhibits protein synthesis of bacteria [McOsker et al, 1994]. Nitrofurantoin is almost completely absorbed, after oral administration. The plasma half-life is 20-30 minutes and is prolonged in renal insufficiency. A rapid metabolism of the drug is produced in tissues. Maximum plasma concentrations only are about 1 mg/L, not reaching effective antibacterial concentrations in plasma and tissues. On the contrary, about 30% of oral administered nitrofurantoin is excreted in urine without biotransformation, reaching levels between 50 and 250 mg/L. This fact justifies its use in infections of low urinary routes, in order to keep aseptic the urinary tract, without compromising normal intestinal flora [Nicolle L., 2002]. However, until the present day, pharmacodynamic studies have not been able to determine clearly the way of metabolism of the 70% of the drug and whether this metabolism can generate toxic metabolites which would contribute to side effects associated with this drug, especially those of systemic effect. The only known evidence of metabolic ways of nitrofurantoin is the enzymatic nitro-reduction by in vitro studies.

Despite its advantages, the use of nitrofurantoin is limited due to the high incidence of adverse effects and also because the continuous use has been associated with systemic damage [Guay D., 2008]. These adverse effects include respiratory dysfunction [Witten C., 1989; Bialas et al, 1997; Goemaere et al, 2008], lung damage [Chudnofsky et al, 1989], liver damage [Penn et al, 1982; Paiva et al, 1992; Rossi et al, 1988], peripheral polyneuropathy [Jacknowitz et al, 1977; Jacknowitz A, 1985], hematological alterations [Gait J., 1990] and gastrointestinal disorders [Brumfitt et al, 1998].

Primarily, it has been postulated that pulmonary and hepatic toxicity in human beings [Martin W., 1983a; Martin W., 1983b; Minchin et al, 1986; Moreno et al, 1984; Rossi et al, 1988; Viode et al, 1999] results from nitro-reduction of nitrofurantoin. This reaction is catalyzed by reductases that could cause gastrointestinal disorders, including nausea, abdominal pain, constipation, dyspepsia and often vomiting and diarrhea [Nitrofurantoin 2005; Brumfitt et al, 1998]. It is postulated that nitro-reduction would be at least one of the causes of adverse effects produced by this drug. Gastrointestinal disorders are the principal cause of discontinuation of nitrofurantoin treatment and hence, the failure of therapy. This is of special relevance when the therapy must be prolonged over extended periods of time (at least six months), as in recurrent UTI treatment.

In addition to microcrystalline nitrofurantoin this drug has been formulated in capsules with enteric coating which delay the absorption. This latter formulation would contribute to a better gastric tolerance, for instance reducing gastrointestinal adverse reactions. However, long-term systemic toxicity is not overcome by this formulation. The low price of microcrystalline nitrofurantoin without enteric coating and low resistance developed against this drug (<6%) in the last ten years in Chile [Cortés et al, 2007], have drive to the Chilean Public Health System to continue its therapeutic and prophylactic prescription, in spite of its association with short and long-term toxicity and to the high probability of discontinuation by the patient, due to the intolerance.

As we mentioned above, side-effects mechanisms of nitrofurantoin are not clear, however nitro-reduction (postulated as one of the causes of adverse effects) is catalyzed by reductases which include reductases from bacterial flora and several hepatic reductases, especially cytochrome P450 (CYP) reductase [Sreider et al, 1990; Bartel et al, 2009; Wang et al, 2008; Lemaire et al, 1994; Pourahmad et al, 2001]. Nitro-reduction of nitrofurantoin proceeds in a futile cycle, generating reactive oxygen species (ROS). These species, if are not controlled by the cell, cause oxidative stress; in these conditions the cellular antioxidant capacity is exceeded, altering functionality of biomolecules, leading to cell damage.

It is well known that in greater or smaller degree, oxidative stress is associated to all pathologies. In this sense, the body defends itself of the pathological states activating immunological system, causing inflammatory processes and the liberation of certain cytokines [Konstan M., 1998]. These processes involve generation of ROS to eliminate damaged biomolecules to repair tissues destroyed in the pathological process.

Enzymatic Nitro-Reduction of Nitrofurantoin

The enzymatic nitro-reduction of nitrofurantoin involves the transference of an electron from donors such as nicotinamide adenine dinucleotide phosphorylated hydrogen (NADPH) to nitrofurantoin, generating a nitro-anion radical ($—NO_2.^-$), which can enter to redox recycling with molecular oxygen, re-generating nitrofurantoin. This "futile cycle" produces superoxide anion ($O_2.^-$), that can dismutate to hydrogen peroxide ($H_2O_2$) and, in the presence of $Fe^{2+}$ or $Cu^+$, generates the hydroxy radical (HO.) [Minchin et al, 1986; Moreno et al, 1984; Rossi et al, 1988; Viode et al, 1999; Letelier et al, 2004]. On the other hand, the $—NO_2.^-$ radical can continue towards formation of nitrous derivatives, hydroxylamine, amine and finally the re-generation of the original nitro compound, again a "futile" cycle [Letelier et al, 2004].

Cellular Response to Oxidative Stress and Antioxidants

In the cell, the activation of molecular oxygen to its radical species $O_2.^-$ and hydroxy radical (.OH), occurs in aerobic conditions. Under physiological conditions, the partial reduction of oxygen to its radical species can occur for example in cytosol, catalyzed by xanthine oxidase; in mitochondria, catalyzed by monoamine-oxidase and in the endoplasmic reticulum, through CYP reductase [Karuzina et al, 2007]. On the other hand, transition metals such as iron and copper, through Haber Weiss/Fenton reaction, can generate ROS [Goldstein et al, 1986].

Nitrogen reactive species are also generated in the organism, but in smaller amount than those of oxygen. These species mainly originate through system nitric oxide synthase producing nitric oxide (NO), which reacts with the superoxide anion to produce peroxynitrite ($ONO^-$).

There is increasing evidence that certain ROSs participate in processes of physiological interest, for example: bactericidal and virucidal actions, vasopressor activity, regulatory effect on the expression of certain genes, etc. As it was mentioned previously, under conditions of excessive generation and/or deficient removal of these species, these cause oxidative modifications of biological macromolecules: lipids, proteins and nucleic acids, causing alterations of their structures and function. This can lead to cellular death [Halliwell et al, 1990].

Cells regulate concentration of ROS through their antioxidant activity in most of organelles by means of enzymatic mechanisms complemented with nonenzymatic molecules. Among the enzymatic mechanisms we can mention include Cu, Zn-superoxide dismutase (Cu, Zn-SOD), catalase [Greenwald R., 1990; Bannister et al, 1991; McCord et al, 2002] and glutathione peroxidase (GSH-Px) [Margis et al, 2008]. Among the nonenzymatic mechanisms there are antioxidant substances such as GSH (reduced glutathione), cystein, vitamin E and vitamin C [Elias et al, 2008; Linster et al, 2007]. The Cu, Zn-SOD catalyzes dismutation of $O_2.^-$ in $H_2O_2$ and water [Bannister et al, 1991; McCord et al, 2002], whereas GSH-Px catalyzes reduction of hydroperoxides and $H_2O_2$ [Margis et al, 2008].

GSH is a key antioxidant for the cell, mainly due to the mM concentration into cytoplasm, its direct antioxidant activity as scavenger of free radicals and its role as cofactor for GSH-Px. The participation of GSH as antioxidant has been demonstrated in cytoplasm, nucleus, mitochondrial matrix and endoplasmic reticulum [Schafer et al, 2001]. Some cellular organelles, like mitochondria and peroxisomes, contain specific antioxidant systems, as manganese superoxide dismutase (Mn-SOD) [McCord J., 2002; Whittaker J., 2000] and catalase [Kirkman et al, 2007], respectively, to face ROS continuously generated in the glucose and fatty acids pathways. Similarly, Cu, Zn-SOD and Mn-SOD catalyzes the dismutation of $O_2.^-$, with a compatible affinity with the high generation of this free radical in mitochondria, in the electron transport chain [McCord J., 2002; Whittaker J., 2000]. In peroxysomes catalase produces the reduction of $H_2O_2$ to water during fatty acids oxidation [Kirkman et al, 2007].

A great variety of processes exist that take place in membrane systems which lead to generation of ROS, among them, biotransformation of drugs, causing lipid peroxidation. Nevertheless, the membrane-located antioxidant cellular mechanisms are rare. Until now, the only reported integral membrane enzyme with antioxidant activity (lipoperoxidase) is the microsomal glutathione S-transferase [Mosialou et al, 1989; Hayes et al, 1991]. In addition, this enzyme in a suicidal action, can link covalently highly electrophilic molecules annulling their toxicity [Hayes et al, 1991; Ketley et al, 1975]. Vitamin E is the main soluble non-enzymatic lipid compound, with activity as scavenger of free radicals, quenching their reactivity [Clarke et al, 2008]. Thus, it is of particular interest to complement these antioxidant mechanisms to help to protect cell membranes of lipid peroxidation, which happens especially under conditions of oxidative stress.

Medicinal and Antioxidant Plants

It is known there are diverse natural preparations, especially those polyphenol-enriched, that have been used as antioxidants in pathologies associated with oxidative stress such as cardiovascular diseases [Middleton et al, 2000; Tak Yee Aw, 2005; Ruel et al, 2005].

Herbal extracts used with therapeutic purposes are constituted by diverse active principles of different physicochemical nature. Among antioxidant included in natural extracts we can mention:

Polyphenols (flavonoids, catechins, anthocyanidins, etc.). These compounds are oxidized by free radicals, giving rise to a more stable radical and therefore, less reactive. It has been demonstrated in vivo that flavonoids induce the activity of GSH-transferase, which participates in detoxification processes to produce covalent conjugates between GSH and xenobiotics highly electrophilic [Middleton et al, 2000].

Ascorbic acid. Its antioxidant action is given by its capacity to bind oxygen radical species and to protect cellular antioxidant defenses; in addition, it regenerates reduced physiological antioxidant species of α-tocopherol and GSH and some nonphysiological (β-carotene).

Isoprenoids. Liposolubles substances distributed in highly lipophilic zones of the cell. They act mainly as antioxidants binding lipoperoxide radicals (ROO.) and $O_2.^-$. In addition, some terpenoids inhibit COX-2 activity [García-Pineres et al, 2001], enzyme induced in inflammatory processes.

Polysaccharides. These compounds in oligomeric or polymeric forms, can link to biological membranes through dipole interactions or hydrogen bonds, causing a physical protection that avoids interaction of oxidants with other biomolecules present in these membranes. An example of this type of interactions is the protective effect that mucilages of the *Opuntia* sp. exert on the gastrointestinal wall [Loro, 1999].

Carboxylic acids. Similar to polyphenols, these compounds chelate transition metals, mainly ionic copper and iron, which are involved in the production of free radicals via Haber Weiss and/or Fenton reactions [Pietta, 2000].

Thiol compounds. There are plants that concentrate particularly thiol compounds, mainly cystein. The ability of thiol groups to bind free radicals in a similar way to phenol compounds is recognized; an example of this type of endogenous compounds is the GSH [Horie et al, 1992].

The concentration of natural antioxidants in extracts depend on many factors, among them the part of the plant (vegetal drug) and the extraction solvent. For that reason it is important to define properly the part of the plant to use and the conditions of the extraction process to prepare natural extracts in order to develop phytopharmaceuticals. In addition, it is necessary to indicate that in scientific literature there do not exist studies of therapeutic doses and the few toxicological studies only refers to lethal dose 50 (LD50).

Effect of Herbal Extracts on Hemogram and Biochemical Profile

Herbal active principles are xenobiotics (exogenous substances to the organism) and could produce adverse and/or toxic reactions depending on the administered dose or can cause immunological response, being observed as an increase of the total leukocytes by an increase in the production of lymphocytes (altering the white series). In addition, while some polyphenols (i.e. flavonoids), are metabolized in the liver, could induce oxidative stress, causing cellular damage in the red series [Perez G., 2003], thus affecting hemogram.

On the other hand, several of the potential adverse reactions associated with xenobiotics are produced through liver biotransformation which can cause quantitative and qualitative changes in their pharmacologic activity. Thus, a pro-drug is biotransformed into its pharmacologically active form and an active drug can be detoxified by this biotransformation. Generally, these reactions lead to more hydrophilic metabolites than the original molecule. Moreover, very reactive metabolites can be generated leading to the alteration of the physiological functions of biomolecules [Sierra et al, 2005; Kanter et al, 2002].

Biotransformation reactions are divided conventionally into phase I and phase II stages [Ioannides C, 2002; Parkinson et al., 2008]. Phase I reactions can be oxidations, reductions or hydrolyses. These reactions expose or introduce a hydrophilic functional group (—OH, —$NH_2$, —SH or —COOH) to link polar endogenous molecules or to be excreted. The main responsible of phase I reactions is the CYP450 oxidative system, mainly located in the hepatic endoplasmic reticulum. Phase II reactions are conjugations of certain functional groups in the drug with polar endogenous molecules like glucuronic acid, glutathione, sulfate, glycine or other amino acids. These reactions are catalyzed by microsomal (UDP-glucuronil transferases), mitochondrial, cytosolic (sulfotransferases, N-acetyltransferases, methyl-transferases) enzymes or some other in several cellular compartments (glutathione-S-transferases). The main phase II reaction is glucuronidation; where a phenol or alcohol hydroxy group binds to glucuronic acid activated as UDPGA (Uridin di-phosphate glucuronosyl acid). These reactions produce highly generally inactive polar biological compounds [Ioannides C, 2002; Parkinson et al., 2008].

Adverse reactions to drugs are defined as "Any type of dangerous or non pleasant detected reaction, coming from an intervention related to the use of medicinal product, which predicts risks for a future administration and deserves its prevention, specific treatment, alteration in the dose or even the definitive withdrawal of the product" [Sierra et al, 2005]. Whether the hepatic metabolism of a xenobiotic generates toxic metabolites, the first affected organ would be the liver, triggering itself an inflammatory process in the tissue. It is the case, for example, of the toxicity of organic solvents (i.e., carbon tetrachloride), which induce oxidative stress by hepatic metabolism causing changes in permeability of hepatocytes and therefore, liberation to the bloodstream of enzymes such as aspartate aminotransferase, alanine aminotransferase, alkaline lactate dehydrogenase and phosphatase. It is for this reason that increased serum levels of these enzymes are accepted as markers of hepatic damage. Furthermore, the serum levels of bilirubin increases because the hepatic metabolism decreases. This is because bilirubin is conjugated in the liver to diglucuronide being excreted by renal route. For that reason bilirubin determination is also useful in the diagnosis of hepatic diseases [Schettini et al, 2005].

As we mentioned previously, 30% of nitrofurantoin administered orally are excreted without changes. Thus, 70% will undergo biotransformation, mainly hepatic. However, kidney is the second more important tissue for xenobiotic biotransformation, therefore, nitro-reduction of nitrofurantoin (causing oxidative stress), could cause both hepatic and renal damage. In this respect, there are several antecedents suggesting that reactive intermediaries are excreted by the kidney affecting renal excretion [Albert et al, 1974]. For instance, blood ureic nitrogen (produced by protein degradation) which increases in renal insufficiency [Kanter et al, 2002] and creatinine (produced by creatine hydrolisis in the skeletal muscle) released constantly to the bloodstream are also useful as markers of renal function. Additionally, the transport systems, as for example ion transporters, located in the cell membrane (calcium, phosphorus, potassium, chloride, etc.) also can be affected by reactive metabolites, altering their urinary excretion and for instance, the serum levels of these ions.

Additionally, nitro-reduction of nitrofurantoin can be catalyzed by reductases of the intestinal bacterial flora, causing local oxidative stress after oral administration of this drug. This mechanism could explain why gastrointestinal adverse effects are firstly observed in patients after oral administration of nitrofurantoin. These effects are considered the main reason in the abandonment of the treatment by patients.

The use of medicinal plants has received special interest in recent years. Internationally, the use of these preparations has been promoted to improve the quality of life of elderly people, whose the cell redox balance is already deteriorated. Moreover, the development of phytopharmaceuticals, considering the traditional uses that native medicine has given to the medicinal plants, has increased to international level and its use as alternative or associated therapy to allopathic drugs is promoted [Hoffman et al, 1992].

BRIEF DESCRIPTION OF THE FIGURES

FIG. 7. Results of the hemogram: Nitrofurantoin plus placebo (group 1) and nitrofurantoin plus capsules of standardized dry extract of matico BG-126 (group 2), are appreciated. Average values obtained from hemogram at beginning of the treatment (day 1) and day 11 (once finalized the treatment), are observed. Significant differences ($p > 0.05$) in the analyzed parameters between groups 1 and 2 were not observed [erythrocyte number, hematocrit, hemoglobin, MCV (mean corpuscular volume), MCH (mean corpuscular hemoglobin), MCHC (mean corpuscular hemoglobin concentration), leukocyte number, neutrophil: segmented, eosinophil, lymphocyte, monocyte, ESR (erythrocyte sedimentation rate), ANC (absolute neutrophil count) and platelet number]. Even more, the values were not statistically different from reference values ($p > 0.05$).

DETAILED DESCRIPTION OF THE INVENTION

Within the plants used with medicinal aims is the *Buddleja globosa* Hope (matico), for which several agronomic studies already exist, both about its composition and/or its active principles. The extracts, especially from their leaves, are used by the native medicine for healing and as anti-inflammatory. This medicinal plant is a Chilean native plant of recognized antioxidant, antiinflammatory and for healing activity [Doll et al, 2003; Hoffmann et al, 1992; Mensah et al, 2001]. The *Buddleja* genus belongs to the Escrofulariales order, which comprises near to 100 species between trees and shrubs of the tropical of America, Asia and Africa. In Chile, two species grow in wild form in hills and gullies, between the Region of Valparaiso and "Los Lagos", *Buddleja suaveolens* Kunth et Bouché and *Buddleja globosa* Hope. Only the latter is used medicinally [Hoffman et al, 1992; Muñoz et al, 2001]. Nevertheless, studies do not exist about the doses to be used. The doses administered to patients are very diverse, thus, they are administered empirically under the popular belief that the natural products are innocuous to the human being.

Composition of *Buddleja globosa* Hope

Among chemical compounds present in this plant the following component have been reported: Flavonoids, Escutelarena, Phenylpropanoids (verbascoside, caffeic acids), Terpenes: Iridoids, Sesquiterpenoids (buddlejinas A, B, C), Diterpene (buddlejona), phenylethanoid Glycoside (angaroside) and Tannins [Muñoz et al, 2001; Pardo et al, 1993, Pardo et al, 1997; Houghton y Hikino, 1989; Liao et al, 1999; Mensah et al, 2000; Vogel et al, 2002]. These compounds arrange in heterogeneous way depending on the different structures of the plant, for example:

In Leaves: Terpenoids, Iridoids (Aucubine), Phenylethanoids (Verbascoside and Echinacoside), Flavonoids (Linarine, luteoline and 6-OH-Luteoline) [Houghton and Mensah, 1999].

In Crust: Diterpens (buddlejona and deoxibuddlejona), Bisditerpene (mayenona), Sesquiterpenes (buddlejina A and buddlejina B), phenolic fatty acid esters [Houghton and Mensah, 1999; Mensah et al, 2000].

In Roots: Terpenoids (dihydrobuddlejina A, buddlejona A and buddlejona B), buddlejina (A, B and C) and zerumbona [Liao et al, 1999].

Pharmacological studies in *Buddleja globosa*

Gastroprotective activity: the crude methanol extract of the leaves of *B. globosa* Hope improve the recovery from gastric ulcer injuries induced by acetic acid [Yáñez, 2001; Stream, 2000].

Antioxidant activity: in isolated compounds of leaves *B. globosa*, in hydroalcoholic or propilenglicolic extracts [Mensah et al, 1998; Mensah et al, 2001; Holst-Schlager y Letelier, 2004].

Analgesic and antiinflammatory activity: lipophilic extract of roots and crust of *B. globosa* inhibits the activity of COX-2 and 5-Lipooxygenase [Liao et al, 1999]. Nevertheless, there are not reported studies that approach dose protocols to use; it is probably because of the belief that natural active principles are innocuous. The alcoholic extract of leaves of *B. globosa* (Buddlejaceae) has a dose-dependent analgesic activity in several models of pain [Backhouse et al, 2008a; Backhouse et al, 2008b]. Finally, using albino mice, administered by topical route, a poaching (in NaCl) of the matico extract at 100 mg/Kg, a rapid decrease in edema was observed in relation to the control group (diclofenac treated mice). Authors conclude it is viable to recommend their use as topical antiinflammatory [Martinez, 1994]. With this fact the use of matico in the Chilean folkloric medicine has been validated (use of matico in treatment of wounds).

Activity on the liver: protective effect of flavonoids and phenylpropide glycosides components have been previously shown [Houghton et al, 1989].

Activity on the skin: water extract of *B. globosa* increases the proliferation of fibroblasts in cultures; this activity can accelerate the healing of wounds [Mensah et al, 1998; Mensah et al, 2001].

Antimicrobial activity: lipophilic extracts of crust of stem of *B. globosa* has an antifungal activity against 3 species of *dermatophytes fungi* (*Trichophyton rubrum, Tricophyton interdigitale* and *Epidermophyton floccosum*). The compounds in this extract were diterpenes (buddlejona), bisditerpen (mayenona) and two sesquiterpenes (buddlejina A and buddlejina B) [Mensah et al, 2000]. In addition, it has been reported that glycosides of *B. globosa* display bactericidal activity [Pardo et al, 1993; Pardo et al, 1997].

Ancestral therapeutic uses: Leaves, stems and roots are used traditionally in respiratory affections, contusions, luxation, conjunctivitis, digestive and hemostatic disorders, as carminative, antidiabetic, sedative, antihemorroidal; in insomnia, eczemas, malaria, as anti-inflammatory for eyes, mouth, skin and mucoses, healing, antiulcerous, also used in hemorrhages, bloody diarrheas, antitusive and expectorant.

Toxicological Studies in *Buddleja globosa*

The toxicity of any compound depends on the administered dose. For example, an increase of 10 times dose of the majority of the allopathic drugs generates severe acute toxicity. In addition, the possible beneficial and/or adverse effects that herbal preparations can cause in the body are alterations of blood homeostasis. In our specific product Buddlejinas A, B and C have shown not to be toxic effects after oral administration of the crude extract up to 2 g/Kg and intraperitoneal up to 600 mg/Kg, in mice [Yañez, 2001]. Other authors have reported cytotoxicity in concentrations greater than 50 µg/mL [Mensah et al, 2001].

Clinical Studies in *Buddleja globosa*

Antiinflammatory and healing activity: It has been shown in animal models, an inhibitory activity of COX-2 and 5-Lipooxygenase, in vitro [Konstan, 1998]. Nevertheless, no mechanisms have been studied.

The inventors of the present application have found that, surprisingly, the treatment with a matico extract decrease considerably the gastrointestinal adverse reactions caused by the oral administration of nitrofurantoin to patients with bacterial infections of low urinary tract. In this regard, the analysis of the literature shows a series of documents related to several species of *Buddleja* and their properties. Of these reports, the authors have considered as closer documents the inventions of KR20100028202 and KR100644773 referred to a species of *Buddleja* from China which shows other therapeutic properties not related to the field of the present invention. Moreover, U.S. Pat. No. 4,855,138 describes a mixture containing an extract (water-oil) of dry leaves of matico (2-35%) and its use against disorders of the skin (acne, psoriasis, burns, etc). The composition contains, in addition to the matico extract, sulfo-derivatives like sulfathiazole (2-15%), alcohol amines, oils and a lipophilic base. Furthermore, it is possible to add an inert pigment as zinc oxide and a fragrance. The procedure for obtaining the extract is not described, but it is not a hydroalcoholic extract neither is directed to solve the technical problem raised in the present invention.

Accordingly, the present application directs to the use and the composition of dry extract of leaves of *Buddleja globose* Hope (matico) for the treatment of the gastrointestinal affections associated to the oral administration of nitrofurantoin (especially in microcrystal formulations) in patients with UTI. In some embodiments, stems are also included in the composition.

In the preferred composition, BG126 capsules are used and each includes 350 mg of extract with a polyphenol concentration not exceeding 18 mg. It should be noted that other pharmaceutical formulations can be prepared including up to a tenfold increase in the polyphenol concentration. Such an increase did not show acute toxicity in rats.

EXAMPLES

The following suitable examples according to the invention are preferred but this does not limit the invention in any way.

Example 1

Botanical Characterization of the Extract

Table 1 summarizes the results obtained by means of a procedure of standard hydroalcoholic extraction of *Buddleja Buddleja globosa* Hope.

TABLE 1

Botanical and chemical characterization of the hydroalcoholic extract of *Buddleja Buddleja globosa* that gave origin to the standardized dry extract BG126
Product: Matico Extract 1:3,8 Date: 11.11.05
Series: 11 962 5 Register N°: **SE-616 Code: 1110031 * B-371

|  | Specification | Analysis |
|---|---|---|
| Botanical characteristics | | |
| Species | *Buddleja globosa* | Fulfill |
| Used part | Leaves | Fulfill |
| Organoleptic characteristics | | |
| Aspect | Liquid | Fulfill |
| Colour | Dark brown | Fulfill |
| Odor | Characteristic | Fulfill |
| Physicochemical characteristics | | |
| pH | 4.0-7.0 | 5.2 |
| Alcoholic grade (15° C.) | N.D. | 59° GL |
| Specific weight (20° C.) | N.D. | 0.913 g/mL |
| Solid residue | N.D. | 4.5% |
| Chemical identification | | |
| Flavonoids | Positive | Fulfill |
| Tannins | Positive | Fulfill |
| Saponins | Positive | Fulfill |
| Reducing sugars | Positive | Fulfill |

Botanical characterization

The characteristics of genus and species of a sample of vegetable material correspond to standard vegetable material for confrontation of samples.
(N.D.: not detected).
Chemical identification The spots of identification in thin layer chromatography of one aliquot of samples are similar to the spots of identification of a standard aliquot.

Quantification of polyphenols of the hydroalcoholic extract of *Buddleja globosa*

| Extract | Total Polyphenols |
|---|---|
| *Buddleja globosa* N° of series 119625 | 30.6 ± 2.36 nmoles catechin/µL extract 116.28 µmoles of catechin/g of vegetable drug |

Example 2

Example of Formulation

A capsule of 250-550 mg contains 250-550 mg of BG-126, standardized dry extract of *Buddleja Buddleja globosa* Hope. The total polyphenols is expressed in mg of catechin by mg extract. The standardized dry extract BG-126 is obtained by dehydrating the liquid extract with maltodextrin by spraying, and then the dry extract is quantified, giving raise to the raw material of the capsules, without any other additive.

Example 3

Administration and Dosage for Urinary Tract Infection

The capsule can be administered in the following affections with the following indicated dosage:
a. Infections of the low urinary tract: 1 capsule every 12 hours
b. Gastrointestinal disorders: 1 capsule every 8 hours

Example 4

Toxicity Studies of *Buddleja globosa* in Rats

The toxicity of the hydroalcoholic extract in male adult rats (*Rattus norvegicus*) of the stock Sprague Dawley was determined. This study consisted in the oral administration of the hydroalcoholic extract of leaves of *Buddleja globosa* (dose: 12 fold greater than the dose advised for the phytopharmaceutical GUG/X® Laboratorios Ximena Polanco Chile S.A.) every 8 hours during 12 days. Significant differences in hemogram parameters (red series and white series) or in biochemical profiles were not observed ($p>0.05$). Similarly, statistically significant differences in the macroscopic parameters (relative weight, longitudinal and cross-sectional axis) and hematoxylin-eosin dyed histological samples of spleen were not observed (number of PALS and germinal centers; diameter and area of the germinal centers). Moreover, any evidence of toxic effects was not observed.

TABLE 2

Scheme of sacrifice of the group (1) and group (2) animals

|  | Control Group (1) | Treated Group (2) |
|---|---|---|
| Day 3 | 1-2-3 | 11-12-13 |
| Day 8 | 4-5-6 | 14-15-16 |
| Day 12 | 7-8-9 | 17-18-19 |

Because the extract does not alter hepatic and renal function of the animals, neither the hemogram or even more, the hepatic metabolism of the active components in the extract were affected, this indicate a low toxicity of the tested extract. Thus, the used dose in this test seems not to produce side effects on the animals and would be, for instance, a safe dose.

Example 5

Example of Use

A double blind randomized clinical assay was performed in women who required treatment due to infection of low urinary tract (positive urocultive, bacterium susceptible to nitrofurantoin). Patients were ambulatory in the Urology Polyclinical of the Clinical Hospital of the University of Chile (HCUCH). Those that fulfilled the inclusion and exclusion criteria signed an informed consent to participate in the study. Patients were distributed randomly in the two following groups:

Group 1: 15 patients treated with 100 mg nitrofurantoin (microcrystals) and one placebo capsule, every 12 hours, by 10 days.

Group 2: 15 patients treated with 100 mg nitrofurantoin (microcrystals) and one capsule of dry extract standardized BG-126 of matico leaves, every 12 hours, by 10 days.

During the treatment, under medical and nursery checkup registers of adverse reactions, hemogram, biochemical profile, urocultive and determination of plasma antioxidant capacity were made. All these results can be observed in FIGS. 2 to 9.

Control of gastrointestinal adverse reactions caused by nitrofurantoin, and nitrofurantoin plus matico extract, showed that combined use of this drug and capsules of matico decrease the frequency and intensity of the analyzed gastrointestinal adverse reactions.

Figure 1:
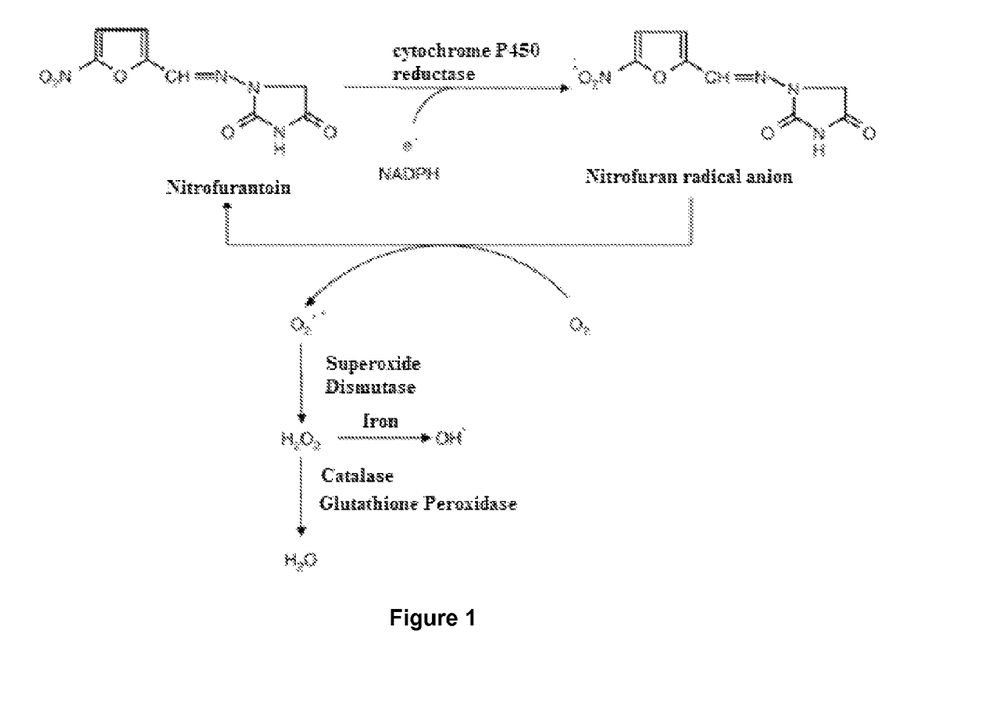
FIG. 1. Redox cycle of nitrofurantoin and generation of ROS (adapted from Wang et al 2008).
Figure 2:
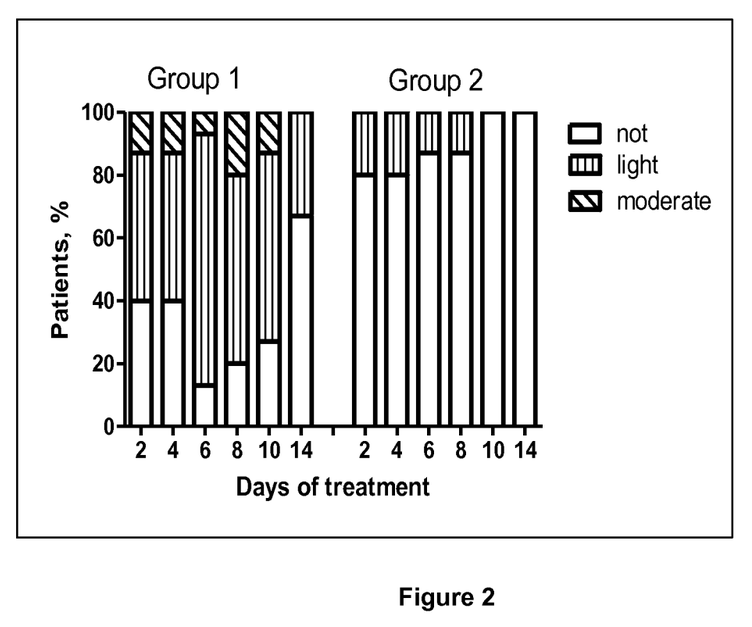
FIG. 2. Results obtained about abdominal pain in the patients. Group 1: nitrofurantoin plus placebo; Group 2: nitrofurantoin plus capsules of dry extract of standardized matico BG-126. Classification of the intensity of the symptoms (no symptoms, light symptoms, moderate symptoms) is described in Table 1. Values represent percentage of patients that displayed the symptom in study; n: 15 patients per group.
Figure 3:
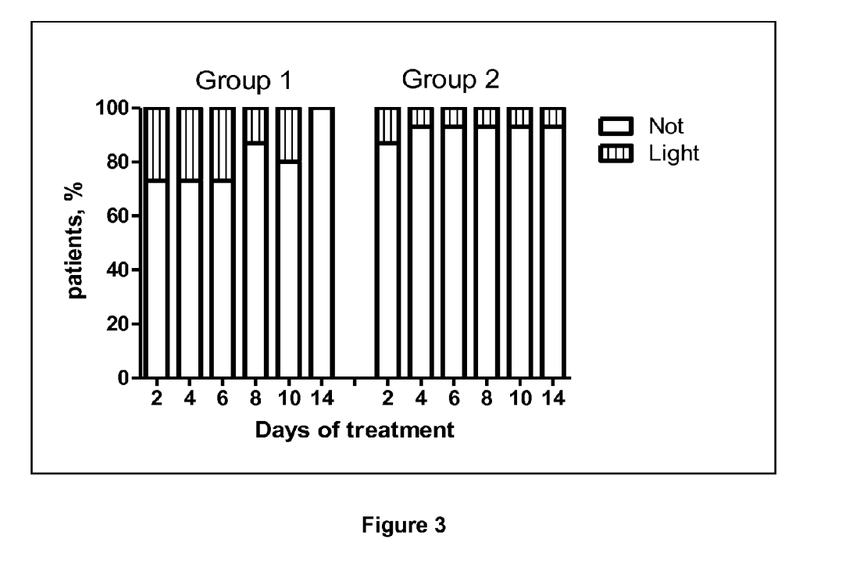
FIG. 3. Results obtained about dyspepsia of patients. Group 1: nitrofurantoin plus placebo; Group 2: nitrofurantoin plus capsules of standardized dry extract of matico BG-126. Classification of the intensity of the symptoms is described in Table 1. Values represent the percentage of patients that displayed the symptom in study, n: 15 patients per group.
Figure 4:
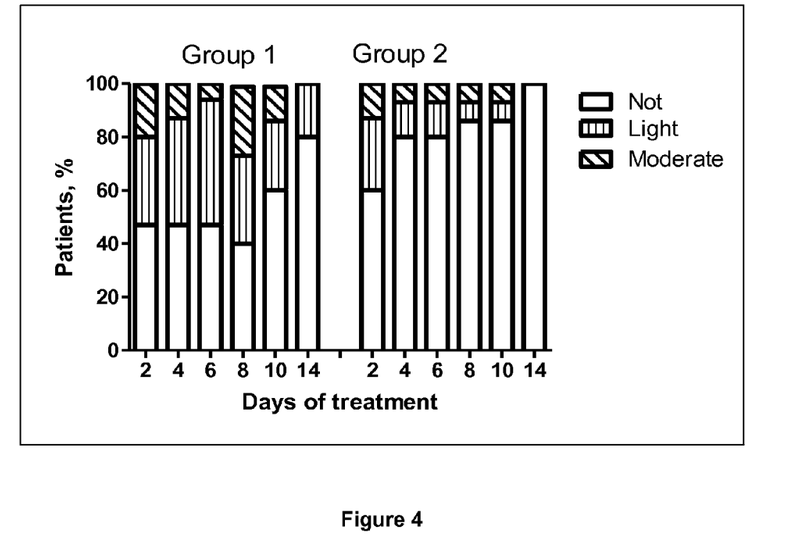
FIG. 4. Results obtained about nausea. Group 1: nitrofurantoin plus placebo; Group 2: nitrofurantoin plus capsules of standardized dry extract of matico BG-126. Classification of the intensity of symptoms is described in Table 1. Values represent percentage of patients that displayed the symptom in study, n: 15 patients per group.
Figure 5:
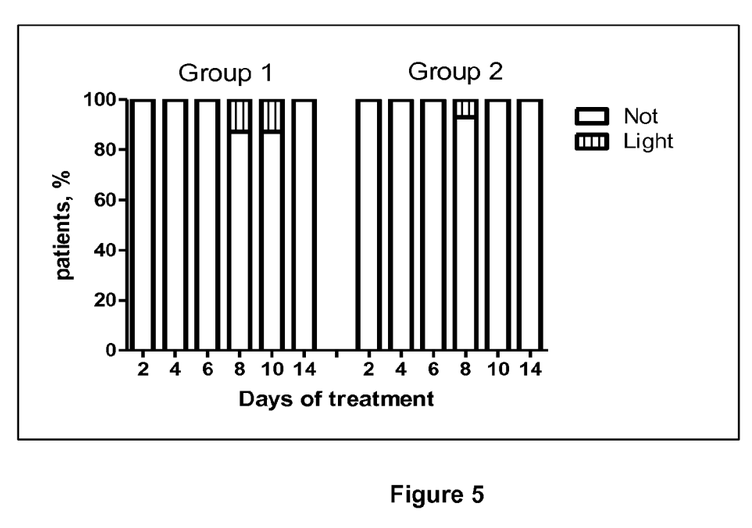
FIG. 5. Results obtained about vomiting. Group 1: nitrofurantoin plus placebo; Group 2: nitrofurantoin plus capsules of standardized dry extract of matico BG-126. Classification of the intensity of the symptoms is described in Table 1. The values represent the percentage of patients that displayed the symptom in study, n: 15 patients per group.
Figure 6:
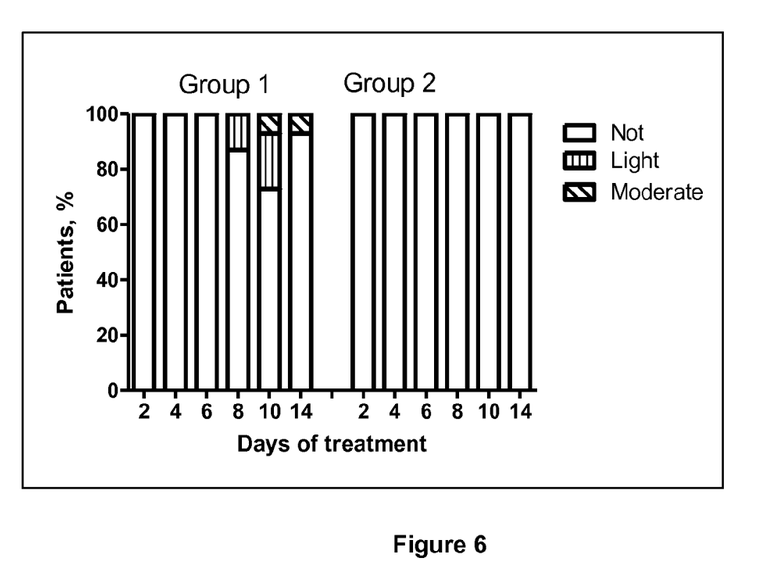
FIG. 6. Results obtained respect to the observation of diarrhea. Group 1: nitrofurantoin plus placebo; Group 2: nitrofurantoin plus capsules of standardized dry extract of matico BG-126. The classification of the intensity of the symptoms is described in Table 1. Values represent the percentage of patients that displayed the symptom in study, n: 15 patients per group.
Figure 7:
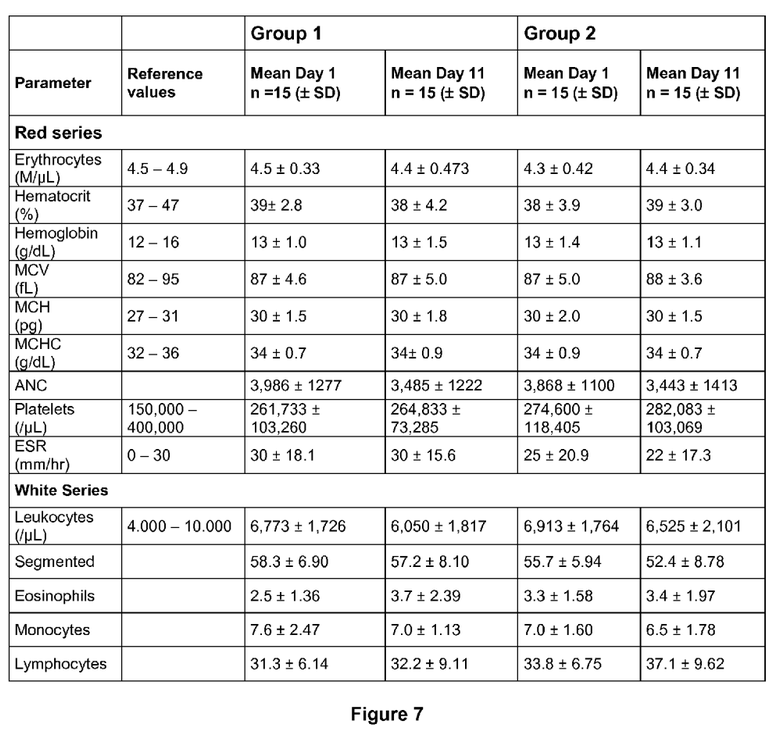
Figure 8:
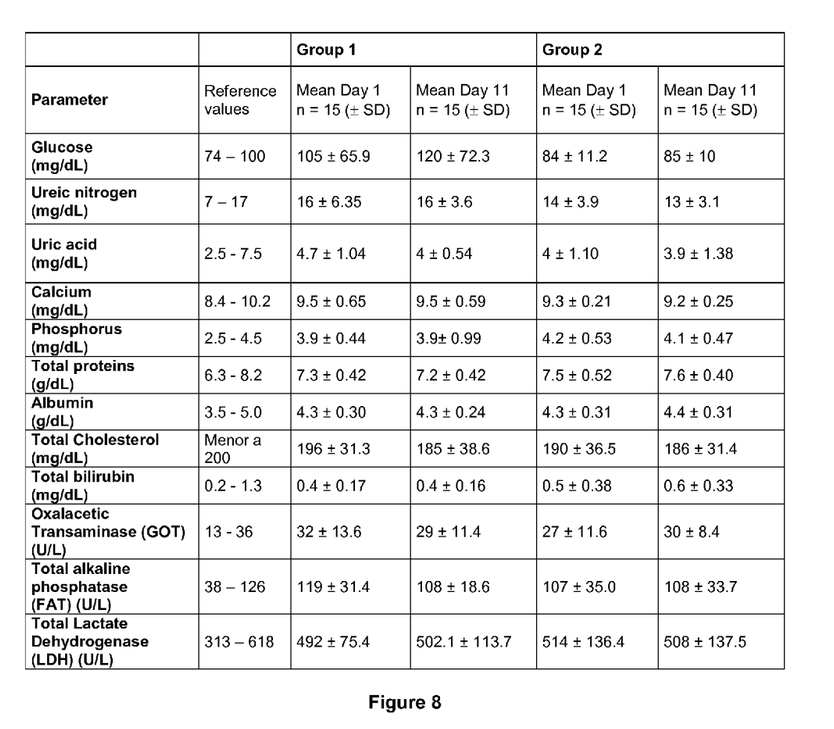
FIG. 8. Results of biochemical profile. Averages values obtained in biochemical profiles performed to the patients of both groups (nitrofurantoin plus placebo and nitrofurantoin plus matico) are appreciated. Results obtained at day 1 (the beginning) and at the end of the treatment (day 11) and the reference values are shown. Significant differences between group 1 and 2 were not observed, in none of the analyzed parameters: glucose, ureic nitrogen, uric acid, total calcium, phosphorus, total proteins, albumin, total cholesterol, total bilirrubin, oxaloacetic transaminase, total alkaline phosphatase, total lactate dehydrogenase ($p > 0.05$). Even more, the values were not statistically different from reference values ($p > 0.05$).
Figure 9:
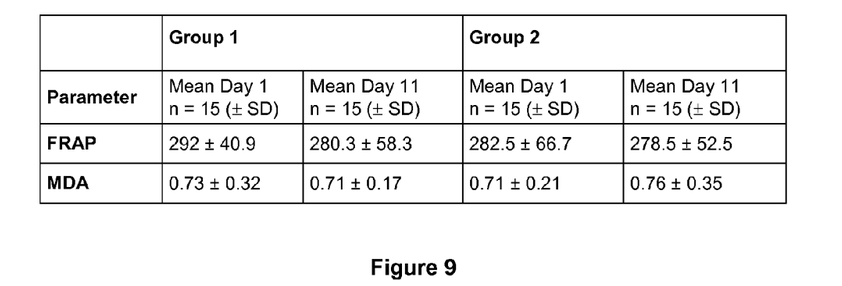
FIG. 9. Results of plasma antioxidant capacity. Averages of results of plasma antioxidant capacity analyses of patients are shown. The evaluated parameters were: ferric reducing ability of plasma (FRAP) and plasma levels of malondialdehyde (MDA). In the table the results of examinations performed at the beginning of treatment (day 1) and once finalized (day 11). For nitrofurantoin plus placebo (group 1) and nitrofurantoin plus capsules of standardized dry extract of matico BG-126 (group 2), at day 1 and day 11 not significant differences were observed between groups (p>0.05).

Significant differences in hemogram, biochemical profile, plasma antioxidant capacity in both groups of patients, were not found, indicating that extract would have preferably local action. Additionally, it is necessary to highlight that 2 patients passed away because of the gastrointestinal adverse reactions. These patients received only nitrofurantoin.

Urocultives done 1 day after finalizing the treatment were negative; nevertheless, one patient who received only nitrofurantoin was positive.

The results of this study allow us to conclude that the concomitant use of nitrofurantoin and matico, represents an alternative treatment for UTI, with lower adverse effects of nitrofurantoin which can allow patients to leave the therapy, especially in patients from primary attention.

REFERENCES

Albert K., Sedman A., Wilkinson P., Stoll R., Murray W. and Wagner J. (1974). Bioavailability Studies of Acetaminophen and Nitrofurantoin. *The Journal of Clinical Pharmacology*, 14: 264-270.

Arroyo J, Quino M, Ronceros S, Oyanguren P, Herrera N y Flores C. (2000). Reporte Preliminar Tratamiento de la úlcera péptica con el micronizado de hojas de *Pipar angustifolium*. Primer Congreso Internacional FITO 2000. Instituto de Fitoterapia Americano. Lima-Perú; pp:175-6.

Backhouse, N., C. Delporte, C. Apablaza, M. Farias, L. Goity, S. Arrau, R. Negrete, C. Castro, and H. Miranda. 2008a. Antinociceptive activity of *Buddleja globosa* (matico) in several models of pain. J Ethnopharmacol 119:160-165.

Backhouse, N., L. Rosales, C. Apablaza, L. Goity, S. Erazo, R. Negrete, C. Theodoluz, J. Rodriguez, and C. Delporte. 2008b. Analgesic, anti-inflammatory and antioxidant properties of *Buddleja globosa*, Buddlejaceae. J Ethnopharmacol 116:263-269.

Bannister W., Bannister J., Barra D., Bond J. and F. Bossa. (1991). Evolutionary aspects of superoxide dismutase: the copper/zinc enzyme. *Free Radic Res Commun*, 12-13pt 1: 349-361.

Bartel L., Montalto de Mecca M. and Castro J. (2009). Nitroreductive metabolic activation of some carcinogenic nitro heterocyclic food contaminants in rat mammary tissue cellular fractions. *Food Chem Toxicol*, 47: 140-144.

Bialas M., Shetty H., Houghton J., Woods F. and Routledge P. (1997). Nitrofurantoin rechallenge and recurrent toxicity. *Postgrad Med J*, 73: 519-520.

Bishop M. (2004). Uncomplicated urinary tract infection. *EUA Update Series*, 2(3): 143-150.

Brumfitt W., Hamilton-Miller J. (1998). Efficacy and safety profile of long therm nitrofurantoin in urinary inffections: 18 years experience. *Journal of Antimicrobial Chemotherapy*, 42: 363-371.

Chudnofsky C. (1989). Otten, E. J. Acute pulmonary toxicity to nitrofurantoin. *Journal of Emergency Medicine*. 17(1): 15-19;

Clarke M., Burnett J. and Croft K. (2008). Vitamin E in human health and disease. *Crit. Rev Clin Lab Sci*, 45: 417-450.

Cortés M., Salazar A., Acuñ a J., Armijo G., López de Santa Marí a J., Berner R., Estrugo A., Riffo C. and Moraga V. (2007). Cambios en la sensibilidad antibiótica de *E. coli* en mujeres con infección urinaria baja ambulatoria en un período de 10 años. *Revista Chilena de Urologia*, 72: 289-291.

Doll U., Vogel H., Jeldres P. and Muñoz M. (2003). Estudios de PropagaciÓn Vegetativa en Matico (*Buddleja globose*). *Ciencia e Investigación Agraria: Revista Latinoamericana de Ciencias de la agriculture*, 30(3): 211-216.

Elias R., Kellerby S. and Decker E. (2008). Antioxidant activity of proteins and peptides. *Crit Rev Food Sci Nutr*, 48: 430-441.

Gait J. (1990). Hemolytic reactions to nitrofurantoin in patients with glucose-6-phosphate dehydrogenase deficiency: theory and practice. *DICP The Annals of Pharmacotherapy*, 24(12): 1210-1213.

Garcí a-Piñeres A., Castro V., Mora G., Schnidt T., Strunck E., Pahl H. and Merfort I. (2001). Cysteine 38 in p65/NF-B plays a crucial role in DNA binding inhibition by sesquiterpene lactones. *J. Biol. Chem*, 276(43): 39713-39720.

Goemaere N., Grijm K., van Hal P. and den Bakker M. (2008). Nitrofurantoin-induced pulmonary fibrosis: a case report. *J Med Case Reports*, 2: 169.

Goldstein S. and Czapski G. (1986). The role and mechanism of metal ions and their complexes in enhancing damage in biological systems or in protecting these systems from these systems from the toxicity of $O_2^-$. *Journal of Free Radicals in Biology & Medicine* 2(1):3-11.

Greenwald R. (1990). Superoxide dismutase and catalase as therapeutic agents for human diseases a critical review. *Free Radical Biology and Medicine*, 8(2): 201-209.

Guay D. (2008). Contemporary management of uncomplicated urinary tract infections. *Drugs*, 68:1169-1205.

Halliwell B. and Gutteridge J. (1990). Role of free radicals and catalytic metal ions in human disease. *Methods in Enzymology*, 186: 1-85.

Hayes P., Bouchier I. and Beckett G. (1991). Glutathione S-transferase in humans in health and disease. *Gut*, 32: 813-818.

Hoffmann A., Farga C., Lastra J. and Veghazi E. (1992). Plantas Medicinales de uso común en Chile. A. Hoffmann, Segunda edición, Ediciones Fundación Claudio Gay, Santiago, Chile.

Holst-Schlager M. and Letelier M. E. (2004). Actividad antioxidante de extractos naturales de uso medicinal: Validación de sistemas biológicos como estándar. XLVII Reunión Anual de la Sociedad de Biologia de Chile. Pucón, 23 al 26 de Noviembre. Libro de Resúmenes, R-112.

Horie T., Awazu S., Itakura Y. and Fuwa T. (1992). Identified diallyl polysulfides from an aged garlic extract which protects the membranas from lipid peroxidation [letter]. *Planta Med*, 58: 468-469.

Houghton P. and Hikino H. (1989). Anti-hepatotoxic activity of extracts and constituents of *Buddleja species. Planta Medica,* 55: 123-6.

Houghton P. and Mensah A. (1999). Biologically-active compounds from *Buddleja* species; En: Romeo J T, ed. Human health protection, nutrition, and plant defense: Recent Advances in Phytochemistry: Phytochemicals. New York: Kluwer Academic/Plenum 33: 343-68.

Ioannides C. (2002). Xenobiotic Metabolism: An Overview. En: Ioannides C, Enzyme systems that metabolise drugs and other xenobiotics (current toxicology), Ed. C. Ioannides. John Wiley y Sons, pp. 1-32.

Jacknowitz A., Le Frock J. and Prince R. (1977). Nitrofurantoin polyneuropathy: report of two cases. *Am J Hosp Pharm,* 34: 759-762.

Jacknowitz A. (1985). Nitrofurantoin ad peripheral neuropathy. *Annals of Internal Medicine,* 102(1): 138-139.

Kanter, Monshouwer M., Meijer D. and Groothuis G. (2002). Precision-Cut Organ Slices as a Tool to Study Toxicity and Metabolism of Xenobiotics with Special Reference to Non-Hepatic Tissues. *Current Drug Metabolism,* (3): 39-59.

Karuzina I. and Archakov A. (1994). The oxidative inactivation of cytochrome P450 in monooxygenase reactions. *Free Radical Biology and Medicine,* 16(1): 73-97.

Ketley J., Habig W. and Jakoby W. (1975). Binding of nonsubstrate ligands to the glutathione S-transferases. *J Biol Chem,* 250: 8670-8673.

Kirkman H. and Gaetani G. (2007). Mammalian catalase: a venerable enzyme with new mysteries. *Trends Biochem Sci,* 32: 44-50.

Konstan, M. (1998). Therapies aimed at airway inflammation in cystic fibrosis. *Clin. Chest. Med,* 19(3): 505-513.

Lee J. and Neild G. (2007). Urinary tract infection. *Medicine,* 35(8): 423-428.

Lemaire P. and Livingstone D. (1994). Inhibition studies on the involvement of flavoprotein reductases in menadione- and nitrofurantoin-stimulated oxyradical production by hepatic microsomes of flounder (*Platichthys flesus*). *Journal of Biochemical Toxicology,* 9: 87-95.

Letelier M. E., lzquierdo P., Godoy L., Lepe A. M. and Faúndez M. (2004). Liver microsomal biotransformation of nitro-aryl drugs: A mechanism for potencial oxidative stress induction. *Journal of Applied Toxicology,* 24(6): 519-525.

Liao Y., Houghton P. and Hoult J. (1999). Novel and known constituents from *Buddleja* species and their activity against leukocyte eicosanoid generation. *J. Nat. Prod,* 62(9): 1241-1245.5.

Linster C. and Van Schaftingen E. (2007). Vitamin C. Biosynthesis, recycling and degradation in mammals. *FEBS J,* 274: 1-22.

Loro J., del Río I. and Perez-Santana L. (1999). Preliminary studies of analgesic and anti-inflamatory properties of *Opuntia dillenii aqueos* extract. *J. Ethnopharmacol,* 67(2): 213-218.

Margis R., Dunand C., Teixeira F. and Margis-Pinheiro M. (2008). Glutathione peroxidase family—an evolutionary overview. *FEBS J,* 275: 3959-3970.

Martin W. J. 2nd. (1983a). Nitrofurantoin: evidence for the oxidant injury of lung parenchymal cells. *Am Rev Respir Dis,* 127: 482-486.

Martin, W. J. 2nd. (1983b). Nitrofurantoin. Potential direct and indirect mechanisms of lung injury. *Chest,* 83: 51S-52S.

MARTINEZ O. (1994). Evaluación farmacológica del efecto antiinflamatorio del preparado de matico. Tesis Fac. Medicina. Universidad Nacional san Antonio Abad del Cuzco—Perú.

McCord J. M. (2002). Superoxide dismutase in aging and disease: an overview. *Methods Enzymol,* 349: 331-341.

McOskar C. and Fitzpatrick P. (1994). Nitrofurantoin: mechanism of action and implications for resistance development in common uropathogens. *Journal of Antimicrobial Chemotherapy,* 33(Suppl A): 23-30.

Mensah A., Houghton P., Bloomfield S., Vlietinck A. and Van den Berghe. (2000). Known and novel terpenes from *Buddleja globosa* displaying selective antifungal activity against dermatophytes. *J Natural Products,* 63(9): 1210-3.

Mensah A., Houghton P., Hughes M. and Chemy G. (1998). In vitro investigation of the wound-healing properties of *Buddleja globosa. Journal of Pharmacy and Pharmacology,* 50: 83.

Mensah A., Sampson J., Houghton P., Hylands P., Westbrook J., Dunn M., Hughes M. and Chemy G. (2001). Effects of *Buddleja globosa* leaf and its constituents relevant to wound healing. *Journal of Ethnopharmacology,* 77(2-3): 219-226.

Middleton E., Kandaswami C. and Theoharides T. (2000). The effects of plant flavonoids on mammalian cells: implications for inflammation, heart disease, and cancer. *Pharmacological Reviews,* 52(4): 673-751.

Minchin R., Ho P. and Boyd M. (1986). Reductive metabolism of nitrofurantoin by rat lung and liver in vitro. *Biochem Pharmacol,* 35: 575-580.

Moreno S., Mason R. and Docampo R. (1984). Reduction of nifurtimox and nitrofurantoin to free radical metabolites by rat liver mitochondria. Evidence of an outer membrane-located nitroreductase. *J Biol Chem,* 259: 6298-6305.

Mosialou E. and Morgenstern R. (1989). Activity of rat liver microsomal glutathione transferase toward products of lipid peroxidation and studies of the effect of inhibitors on glutathione-dependent protection against lipid peroxidation. *Arch Biochem Biophys,* 275: 289-294.

Muñoz O., Montes M. and Wilkomirsky T. (2001). Plantas medicinales de use en Chile—Química y farmacologí a. Santiago de Chile: Editorial Universitaria, pp. 69-72.

Nicolle L. (2002). Urinary tract infection: traditional pharmacologic therapies. *The American Journal of Medicine,* 113(1): 35-44.

Nitrofurantoin, Adverse Effects. In: Sweetman, S. C (Editor). Martindale: the complete drug reference. 34$^a$edición. (2005). Pharmaceutical Press, Londres, pp. 237.

Paiva L., Wright P. and Koff R. (1992). Long-term hepatic memory for hypersensitivity to nitrofurantoin. *Am J Gastroenterol,* 87: 891-893.

Pardo F., Perich F. and Torres R. (1997). Un nuevo glicósido de *Buddleja globosa* con actividad bactericida. *Bol. Soc. Chil. Quim,* 42 (1): 101-104.

Pardo F., Perich F., Villarroel L. and Torres R. (1993). Isolation of verbascoside, an antimicrobial constituent of *Buddleja globosa* leaves. *J Ethnopharmacol,* 39: 221-222.

Parkinson A. and Ogilvie B. (2008). Biotransformation of Xenobiotics. En: Cassaret y Doull's, Toxicology, 7a edición, McGraw-Hill, New York, USA, pp. 161-305.

Penn R. and Griffin J. (1982). Adverse reactions to nitrofurantoin in the United Kingdom, Sweden, and Holland. *Br Med J (Clin Res Ed),* 284: 1440-1442.

Pérez G. (2003). Los flavonoides: antioxidantes o prooxidantes. *Rev. Cubana Invest. Biomed.* 22(1):48-57.

Pietta, P. (2000). Flavonoids as antioxidants. *J Nat Prod,* 63: 1035-1042,

Pourahmad J., Khan S, and O'Brien P. (2001). Lysosomal oxidative stress cytotoxicity induced by nitrofurantoin redox cycling in hepatocytes. *Advances in Experimental Medicine and Biology*, 500: 261-265.

Richards C. (2004). Urinary tract infections in the frail elderly: issues for diagnosis, treatment and prevention. *Int Urol Nephrol*, 36:457-463.

Rossi L., Silva J., McGirr L. and O'Brien P. (1988). Nitrofurantoin-mediated oxidative stress cytotoxicity in isolated rat hepatocytes. *Biochemical Pharmacology*, 37: 3109-3117.

Ruel G., Pomerleau S., Couture P., Lamarche B. and Couillard C. (2005). Changes in plasma antioxidant capacity and oxidized low-density lipoprotein levels in men after short-term cranberry juice consumption. *Metabolism*, 54: 856-861.

Schafer F. and Buettner G. (2001). Redox environment of the cell as viewed through the redox state of the glutathione disulfide/glutathione couple. *Free Radic Biol Med*, 30: 1191-1212.

Schettini L., Li E., Gálvez H., Montoya E. and Sánchez N. (2005). Perfil bioquímico sanguíneo hepático y renal en el sajino (*Tayassu tajacu*) criado en cautiverio en la amazonia peruana. *Rev. Inv. Vet. Perú*, 16(2): 175-179.

Sierra F. and Torres D. (2005). Enfermedad hepática tóxica inducida por drogas: Revisión sistemática estructurada. *Rev. Colombiana Gastroenterología*, 20(1).

Sreider C., Grinblat L. and Stoppani A. (1990). Catalysis of nitrofuran redox-cycling and superoxide anion production by heart lipoamide dehydrogenase. *Biochemical Pharmacology*, 40: 1849-1857.

Tak Yee Aw. (2005). Intestinal glutathione: determinant of mucosal peroxide transport, metabolism, and oxidative susceptibility. *Toxicology and Applied Pharmacology*, 204: 320-328.

Valdebenito J. (2008). Infección urinaria recurrente en la mujer. *Rev Chilena Infectol*, 25: 268-276.

Viode C., Bettache N., Cenas N., Krauth-Siegel R., Chauviere G., Bakalara N., and Perie J. (1999). Enzymatic reduction studies of nitroheterocycles. *Biochem Pharmacol*, 57: 549-557.

Vogel H., Razmilic I., Doll U. and San Martín J. (2002). Domestication Studies in Matico (*Buddleja globosa* Hope). *Acta Horticulturae*, 576: 203-6.

Wang Y., Gray J., Mishin V., Heck D., Laskin D. and Laskin J. (2008). Role of cytochrome P450 reductase in nitrofurantoin-induced redox cycling and cytotoxicity. *Free Radic Biol Med*, 44: 1169-1179.

Whittaker J. (2000). Manganese superoxide dismutase. *Met Ions Biol Syst*, 37: 587-611.

Witten C. (1989). Pulmonary toxicity of nitrofurantoin. *Arch Phys Med Rehabil*, 70: 55-57.

Yáñez T. (2001). Matico, otro arbusto chileno con potencial exportador: Efecto de la infusión de hojas de matico en la úlcera gástrica. Talca: Memoria Instituto de Biología Vegetal y Biotecnología, Universidad de Talca.

The invention claimed is:

1. A method of treating gastrointestinal disorders caused by antimicrobial agents in a human in need thereof comprising administering a capsule containing 250 mg-550 mg of a dry standardized extract of *Globosa buddleja* to said human in need thereof to treat the gastrointestinal disorder in said human.

2. The method according to claim 1 wherein said extract is dry.

3. The method according to claim 2 wherein the extract contains less than 5% water.

4. The method according to claim 1 wherein the gastrointestinal disorder is associated with nitrofurantoin treatment.

5. The method according to claim 1 wherein said gastrointestinal disorder is produced by ulcers, gastric pathologies or damage to the gastric apparatus.

6. The method according to claim 1 wherein said gastrointestinal disorder includes symptoms of any of abdominal pain, dyspepsia, nausea, vomiting, diarrhea, constipation, inflammation and cephalea.

7. The method according to claim 1 wherein said method is further used to potentiate antibacterial action of nitrofurantoin.

8. The method according to claim 7 wherein said antibacterial action of nitrofurantoin is against *Escherichia coli*.

9. The method according to claim 1 wherein content of said capsule is solid or liquid.

10. The method according to claim 1 wherein the content of said capsule is a water solution, a syrup or a suspension.

* * * * *